US008680073B2

(12) United States Patent
Chang et al.

(10) Patent No.: US 8,680,073 B2
(45) Date of Patent: *Mar. 25, 2014

(54) STABLE HYALURONAN/STEROID FORMULATION

(75) Inventors: Grace Chang, Brookline, MA (US);
Elizabeth Voschin, Needham, MA (US);
Li-Ping Yu, Ashland, MA (US); Eugene Skrabut, Rockport, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/593,026

(22) Filed: Aug. 23, 2012

(65) Prior Publication Data

US 2012/0316131 A1    Dec. 13, 2012

Related U.S. Application Data

(62) Division of application No. 12/556,869, filed on Sep. 10, 2009, now Pat. No. 8,273,725.

(51) Int. Cl.
*A61K 31/58* (2006.01)
*A61K 31/728* (2006.01)
*A61P 19/02* (2006.01)
*A61P 29/00* (2006.01)

(52) U.S. Cl.
USPC ............................. 514/54; 514/174; 424/443

(58) Field of Classification Search
None
See application file for complete search history.

(56) References Cited

U.S. PATENT DOCUMENTS

| | | | | |
|---|---|---|---|---|
| 4,425,344 | A | * | 1/1984 | Horlington ............... 514/249 |
| 4,851,521 | A | | 7/1989 | DellaValle et al. |
| 4,866,050 | A | | 9/1989 | Ben-Amoz |
| 4,957,744 | A | | 9/1990 | DellaValle et al. |
| 5,207,983 | A | * | 5/1993 | Liebert et al. ............... 422/25 |
| 5,234,914 | A | | 8/1993 | Gallina |
| 5,356,883 | A | | 10/1994 | Kuo et al. |
| 5,616,568 | A | | 4/1997 | Pouyani et al. |
| 5,621,093 | A | | 4/1997 | Swann et al. |
| 5,644,049 | A | | 7/1997 | Giusti et al. |
| 5,676,964 | A | | 10/1997 | DellaValle |
| 5,985,850 | A | | 11/1999 | Falk et al. |
| 6,066,292 | A | | 5/2000 | Purwar |
| 6,096,727 | A | | 8/2000 | Kuo et al. |
| 6,197,326 | B1 | | 3/2001 | Suzuki et al. |
| 6,392,036 | B1 | | 5/2002 | Karlsson et al. |
| 6,428,804 | B1 | | 8/2002 | Suzuki |
| 6,521,223 | B1 | | 2/2003 | Calias et al. |
| 6,726,918 | B1 | | 4/2004 | Wong et al. |
| 6,863,865 | B2 | | 3/2005 | McAffer et al. |
| 6,891,035 | B2 | | 5/2005 | Ljungquist |
| 7,309,497 | B2 | | 12/2007 | Rimpler et al. |
| 2006/0094700 | A1 | | 5/2006 | Lyons |
| 2006/0141049 | A1 | | 6/2006 | Lyons et al. |
| 2008/0044476 | A1 | | 2/2008 | Lyons et al. |
| 2009/0143348 | A1 | | 6/2009 | Tezel et al. |

FOREIGN PATENT DOCUMENTS

| | | |
|---|---|---|
| EP | 1710257 | 10/2006 |
| WO | 2005/066215 | 7/2005 |
| WO | 2007/070547 | 6/2007 |
| WO | 2009/024670 | 2/2009 |
| WO | 2009/095790 | 6/2009 |

OTHER PUBLICATIONS

Jones, A., A double-blind trial of intra-articular (i.a.) hyaluronic acid (HA) vs. (i.a.) triamcinolone hexacetonide (TH) in knee osteoarthritis (OA), Osteoart and Cartil. vol. 1, Issue 1:71, 1993.
Jones et al., Intra-articular hyaluronic acid compared to intra-articular triamcinolone hexacetonide in inflammatory knee osteoarthritis, Osteoarthritis and Cartilage, Bailliere Tindall, London, GB, vol. 3, No. 4, pp. 269-273 (Dec. 1995).
Maheu, E., et al., A Hyaluronan Preparation (500-730 KDA) in the Treatment of Osteoarthritis: A Review of Clinical Trials with Hyalgan (R), Int. Jour. Of Clinical Practice, Medicon International, Esher, GB, vol. 56, No. 10, pp. 804-813 (Jan. 2002).
Nizolek, Donna J., et al., Corticosteroid and Hyaluoronic Acid Treatments in Equine Degenerative Joint Disease A Review, New York State College of Veterinary Medicine, Guest Editorial (1981).
Rydell, Nils, et al., Effect of Intra-articular Injection of Hyaluronic Acid on the Clinical Symptoms of Osteoarthritis and on Granulation Tissue Formation, Clinical Orthopaedics and Related Research, No. 80, Oct. 1971.
Rydell, Nils, et al., Hyaluronic Acid in Synovial Fluid, Acta vet. scand. 1970, 11, 139-155.
Supplementary European Search Report from corresponding European Application No. 10815804 dated Sep. 26, 2012.
Yu et al., Osteoarthritis and Cartilage, vol. 12, Supp. B, p. 350 (2004).

* cited by examiner

*Primary Examiner* — Leigh Maier
(74) *Attorney, Agent, or Firm* — Fish & Richardson P.C.

(57) ABSTRACT

A pharmaceutical composition comprising in admixture a hyaluronic acid related component (HARC) and a pharmaceutically effective amount of triamcinolone hexacetonide (TAH). The composition is stable in an accelerated shelf life test in which the composition is heated to 80° C. for 24 hours.

10 Claims, 3 Drawing Sheets

STABLE HYALURONAN/STEROID FORMULATION

CROSS-REFERENCE TO RELATED APPLICATIONS

This application is a divisional application of and claims priority to U.S. application Ser. No. 12/556,869, filed on Sep. 10, 2009 now U.S. Pat. No. 8,273,725.

TECHNICAL FIELD

This invention is in the general field of compositions and methods comprising hyaluronic acid (HA) or an HA-related component (collectively "HARC"), for example pharmaceutical compositions, devices and methods for treating various medical conditions.

BACKGROUND

Hyaluronic acid has many medical uses, and various HARCs have been developed. The term HARC includes hyaluronic acid itself (including HA from living sources such as avian or bacterial sources), as well as hyaluronic acid salts and derivatives of the foregoing, including polymerized gels, cross-linked gels, and derivatized hyaluronic acid.

HARCs may be administered by themselves, for example to provide relief from arthritis. They also may be mixed with anti-inflammatory steroids. Lyons US2006/0141049 discloses pharmaceutical compositions containing triamcinolone acetonide and hyaluronate. Yu et al., *Osteoarthritis and Cartilage* vol. 12, Supp. B, P350 at page S144 (2004) discloses an in vitro evaluation of hylan G-F 20 diluted with a corticosteroid (triamcinolone acetonide) suspension.

When used in a medical product HARCs typically are sterilized by heating, autoclaving, chemical treatment or filtration. Often it is important to maintain the viscoelastic properties of the HARC. Sterilization techniques may alter viscoelastic properties or make it difficult to control or maintain the stability of those properties. Sterilization may decrease the shelf life of the product.

In some cases, HARCs are heat sterilized before forming a steroid/HARC mixture. Sterility of the final mixture may be achieved by filtration of the steroid solution before it is mixed with the HARC.

SUMMARY

We have discovered that, when mixed with an HARC, one particular steroid salt, triamcinolone hexacetonide (TAH), retains its chemical integrity and provides a stable pharmaceutical composition with suitable shelf life and stability (particularly viscoelastic stability after sterilization) as compared to the original HARC (without the TAH). These and other properties provide a more efficient and convenient formulation. The combined composition shows good stability during and after heat sterilization in comparison to controls.

Accordingly one aspect of the invention can be generally stated as a pharmaceutical composition comprising in admixture a hyaluronic acid related component (HARC) and a pharmaceutically effective amount of triamcinolone hexacetonide (TAH). The composition is stable in an accelerated shelf life test in which the composition is heated to 80° C. for 24 hours. Preferably, after this shelf life test, a) the % change of one or more viscoelastic properties (elastic modulus $\Delta G'$, viscosity $\Delta\eta$, and/or phase angle $\Delta\delta$) should be no more than $\forall 10\%$ as compared to the comparable change in the control HARC (without TAH); b) the change in the composition pH should be no more than 0.5 pH unit; c) the change in osmolarity should be less than 10% (more preferably less than 5%) different from the change in osmolarity of the control HARC; d) the steroid should retain at least 90% (more preferably at least 95%) of its chemical integrity—i.e., there is less than 10% (more preferably less than 5%) chemical degradation—as determined by recovery data. Examples of suitable protocols for shelf-life and other tests are provided below.

Preferably the composition can be heat sterilized. For example, the composition is stable in a simulated autoclave conditions with approximate 30 $F_o$, in which the composition is heated at 121° C. for 30 min in a oil bath. Preferably, after the heat sterilization, the % change of G', viscosity ($\eta$) or phase angle ($\delta$) should be no more than 20% different (more preferably no more than 15% different) from the control (HARC without TAH);

While the invention includes HARCs that are 100% gel or fluid, in preferred embodiments of this aspect of the invention, the HARC component includes both a cross-linked HARC gel and an HARC fluid component. The combination has a gel:fluid ratio between 80% and 20%, more preferably between 65% and 35%. Other HARCs may be used, including Orthovisc®, Monovisc™, Cingal™, and Elevess™ dermal filler (all from Anika Therapeutics), Adant, Arthrease, Arthrum, Durolane, Fermathron, Go-on, Hya-ject, Hyalgan/Hyalart, Hyalubrix, Hy-GAG, Ostenil, Sinovial, Supartz/Artz, Suplasyn, Synochrom, Viscorneal, Enflexxa, and Geleo.

Preferably one ml of the composition includes at least 5 mg HA, when measured by standard procedures such as acid degradation followed by a determination of the HA free acid.

The composition has a viscosity and an extrusion force that enable its use in a syringe. For example, it is delivered from a 5 cc syringe with a needle size of 20G-1.5" with an extrusion force of less than 30 Newtons. The viscosity is between 20 Pas and 100 Pas.

The gel component may be divinyl sulfone (DVS) cross-linked hyaluronic acid.

The composition may be packaged in a syringe for delivery to a patient and it has a sterility assurance level (SAL) suitable for human administration.

In some embodiments, the composition includes a surfactant, such as Polysorbate 80, Polysorbate 20, Pluronic F-127, Pluronic F-68 or other physiologically suitable surfactants.

The stability provided by the invention enables a longer shelf life at room temperature so that the mixture may be stored after heat sterilization. The sterilized mixture can be packaged and stored (e.g., in a syringe) for later use. Accordingly, another aspect of the invention features a package containing a syringe filled with the sterilized pharmaceutical composition.

The invention also provides more efficient manufacturing methods, and another aspect of the invention can be generally stated as a method of making the above described sterilized pharmaceutical composition by mixing the HARC with the TAH, and subjecting the mixture to heat sterilization. The sterilized mixture is then stored under sterile conditions.

The invention may be used in a method of treating a patient for joint disease by using the syringe to administer the pharmaceutical composition into a joint of the patient. Administration may be by standard injection, by introduction on-site during arthroscopic surgery or open-knee surgery.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
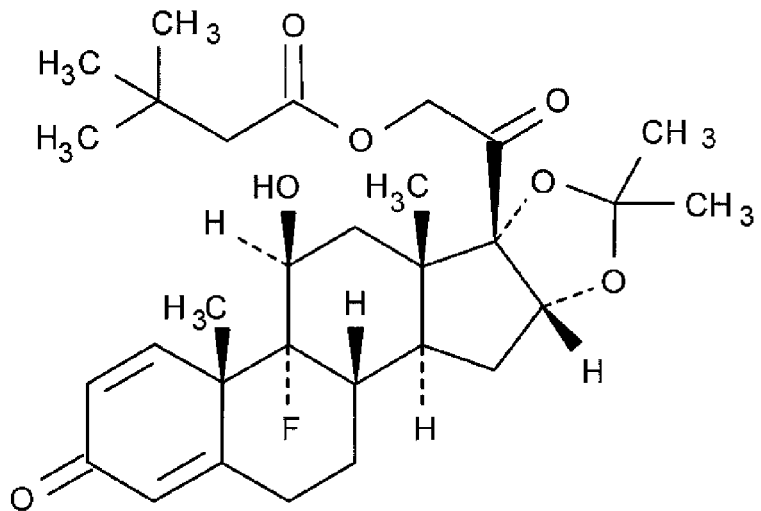
FIG. 1 shows the structure of TAH.

One embodiment of the invention combines: a) a cross linked HA-gel; b) a modified or unmodified HA fluid and c) the insoluble steroid triamcinolone hexacetonide (TAH).

Various procedures for HA cross linking are known, for example divinyl sulfone cross-linked HA as described in US2005 0142152, U.S. Pat. No. 5,143,724 and U.S. Pat. No. 4,582,865, each of which is hereby incorporated by reference. Other suitable cross linking agents may be used in place of DVS. For example, formaldehyde, glutaraldehyde, glyoxal, (U.S. Pat. No. 4,713,448); 1,4 butane diol diglycidylether (BDDE) 1,4-butane diol diglycidylether (BDDE), 1,2-ethandioldiglycidylether (EDDE), 1-(2,3-epoxypropyl)-2,3, epoxycyclohexane, N,N-diglycidylaniline, epoxysubstituted pentaerythritol (U.S. Pat. No. 4,772,419); biscarbodiimides such as p-phenylene-bis(ethylcarbodiimide) (U.S. Pat. No. 6,548,081); epichlorohydrin (WO8600079); polyaziridines, such as pentaerythritol tris(3-aziridinopropionate) (XAMA-7) (U.S. Pat. No. 5,827,937 and US2005-0222081). Each of the above references is hereby incorporated by reference.

Formulations according to the invention are stable to an autoclave sterilization process. Additionally, the formulations are stable when subjected to accelerated stability tests such as a simulated two-year room temperature storage condition. Stability (as determined by rheology) of triamcinolone hexacetonide/viscosupplement combinational formulations compare favorably with formulations that replace the triamcinolone hexacetonide with a very similar steroid, triamcinolone acetonide (TAA). These two steroids are very similar chemically and a significant difference in stability would not be predicted.

We conducted various experiments in which a number of steroids, both soluble and insoluble, were mixed with HA-based viscosupplements, and the heat stability of the HA/steroid formulations were evaluated at 121° C. for 30 min (simulated autoclave conditions), to achieve a bioburden inactivation of approximate 30 $F_o$, where $F_o$ is the total heat applied during the cycle to achieve a desired probable inactivation ratio). Formulations were also evaluated after heating at 80° C. for 24 hours (simulated two year room temperature shelf-life).

Viscosupplements containing triamcinolone hexacetonide (TAH) generally exhibited stability comparable to a viscosupplement control (the same formulation with no steroid) within the limits described. Other steroid/viscosupplement combinations we tested demonstrated a decrease in HA stability as determined by rheology.

Rheological Properties

Specifically we tested the TAH mixtures with SYNVISC® and hylastan products of Genzyme Corporation, Framingham Mass.[1] The rheological properties of the heat treated SYNVISC®/steroid and hylastan SGL-80/steroid formulations plus their controls are listed in Tables 1a and 1b, respectively, set out below.

[1] Synvisc is a gel-like mixture that is made up of hylan A fluid, hylan B gel, and salt water. Hylan A and hylan B are made from a substance called hyaluronan (also known as sodium hyaluronate) from chicken combs.

TABLE 1a

Rheology Results of Synvisc/Steroid Formulations by Heat Treatment

| Sample ID | Name of Steroid | Heat Treatment | G' (Pa) | St. Dev | % G' heat | DG' (%) | h (Pas) | St. Dev | % h heat | Dh (%) |
|---|---|---|---|---|---|---|---|---|---|---|
| Synvisc Ctrl | No Steroid | No Heat | 126 | 6.4 | | | 60 | 0.7 | | |
| | | 80° C./24 hr | 101 | 0.0 | 80.5% | 0.0% | 38 | 0.0 | 63.9% | 0.0% |
| Synvisc - S | Betamethasone Phosphate | No Heat | 121 | 2.8 | | | 59 | 1.4 | | |
| | | 80° C./24 hr | 18 | 0.0 | 14.9% | −65.6% | 2 | 0.1 | 3.4% | −60.5% |
| Synvisc - K | Triamcinolone Acetonide | No Heat | 112 | 0.7 | | | 61 | 0.0 | | |
| | | 80° C./24 hr | 9 | 1.1 | 7.8% | −72.7% | 0.9 | 0.1 | 1.4% | −62.5% |
| Synvisc - D | Methylprednisolone Acetate | No Heat | 118 | 9.9 | | | 61 | 2.8 | | |
| | | 80° C./24 hr | 22 | 1.4 | 18.6% | −61.9% | 2.8 | 0.1 | 4.6% | −59.3% |
| Synvisc - C | Betamethasone Acetate | No Heat | 129 | 4.9 | | | 63 | 2.1 | | |
| | | 80° C./24 hr | 1111 | 211 | 864.6% | 784.1% | 69 | 2.1 | 109.6% | 45.7% |
| Synvisc - A | Triamcinolone Hexacetonide | No Heat | 120 | 7.1 | | | 65 | 0.7 | | |
| | | 80° C./24 hr | 100 | 1.4 | 83.3% | 2.8% | 37 | 0.7 | 56.6% | −7.3% |

% $X_{heat}$ = 100% * X(post-heat)/X(pre-heat);
ΔX = % $X_{heat}$(HARC/Steroid) − % $X_{heat}$(HARC/Ctrl);
In which X = G' or η

TABLE 1b

Rheology Results of hylastan SGL-80/Steroid Formulations by Heat Treatments

| Sample ID | Name of Steroid | Heat treatment | G' (Pa) | St. Dev | % G' heat | DG' % | d(°) | St. Dev | % d heat | Dd (%) | h (Pas) | St. Dev | % h heat | Dη (%) |
|---|---|---|---|---|---|---|---|---|---|---|---|---|---|---|
| Hylastan Ctrl | No Steroid | No Heat | 126 | 4.9 | | | 16 | 0.7 | | | 102 | 0.7 | | |
| | | 121° C./30 min | 74 | 0.7 | 58.6% | 0.0% | 24 | 0.0 | 154.8% | 0.0% | 57 | 0.7 | 56.1% | 0.0% |
| | | 121° C./30 min & 80° C./24 h | 57 | 1.4 | 77.6% | 0.0% | 28 | 1.4 | 116.7% | 0.0% | 47 | 4.2 | 76.5% | 0.0% |

TABLE 1b-continued

Rheology Results of hylastan SGL-80/Steroid Formulations by Heat Treatments

| Sample ID | Name of Steroid | Heat treatment | G' (Pa) | St. Dev | % G' heat | DG' % | d(°) | St. Dev | % d heat | Dd (%) | h (Pas) | St. Dev | % h heat | Dη (%) |
|---|---|---|---|---|---|---|---|---|---|---|---|---|---|---|
| Hylastan - S | Betamethasone Phosphate | No Heat | 123 | 4.9 | | | 16 | 0.7 | | | 92 | 5.7 | | |
| | | 121° C./30 min | 21 | 7.1 | 17.1% | −41.5% | 39 | 3.5 | 248.4% | 93.6% | 20 | 7.9 | 16.4% | −39.7% |
| | | 121° C./30 min & 80° C./24 h | 4.1 | 0.1 | 19.3% | −58.3% | 50 | 0.0 | 129.9% | 13.2% | 1.4 | 0.1 | 9.0% | −67.5% |
| Hylastan - K | Triamcinolone Acetonide | No Heat | 129 | 0.0 | | | 15 | 0.0 | | | 98 | 0.7 | | |
| | | 121° C./30 min | 2.5 | 1.0 | 1.9% | −56.7% | 53 | 4.9 | 350.0% | 195.2% | 0.8 | 0.3 | 0.6% | −55.5% |
| | | 121° C./30 min & 80° C./24 h | 1.6 | 0.1 | 62.0% | −15.6% | 47 | 2.8 | 89.5% | −27.2% | 0.1 | 0.0 | 13.3% | −63.2% |
| Hylastan - D | Methyl prednisolone Acetate | No Heat | 134 | 2.1 | | | 16 | 0.7 | | | 114 | 10.6 | | |
| | | 121° C./30 min | 8.9 | 0.8 | 6.7% | −51.9% | 45 | 0.7 | 287.1% | 132.3% | 3.4 | 0.2 | 3.3% | −52.8% |
| | | 121° C./30 min & 80° C./24 h | 3.5 | 0.4 | 39.3% | −38.3% | 53 | 3.5 | 118.0% | 1.3% | 1.3 | 0.3 | 42.3% | −34.2% |
| Hylastan - C | Betamethasone Acetate | No Heat | 139 | 0.0 | | | 15 | 0.0 | | | 117 | 0.7 | | |
| | | 121° C./30 min | 107 | 11.3 | 77.0% | 18.4% | 23 | 0.7 | 150.0% | −4.8% | 77 | 2.1 | 67.4% | 11.3% |
| | | 121° C./30 min & 80° C./24 h | 104 | 2.8 | 97.2% | 19.6% | 22 | 0.0 | 97.8% | −18.9% | 41 | 3.5 | 55.4% | −21.1% |
| Hylastan - A | Triamcinolone Hexacetonide | No Heat | 145 | 5.7 | | | 16 | 0.7 | | | 111 | 2.1 | | |
| | | 121° C./30 min | 86 | 2.8 | 59.3% | 0.7% | 23 | 0.7 | 145.2% | −9.6% | 79 | 2.8 | 68.4% | 12.3% |
| | | 121° C./30 min & 80° C./24 h | 65 | 1.4 | 75.6% | −2.0% | 27 | 0.0 | 120.0% | 3.3% | 57 | 0.7 | 74.7% | −1.8% |

% $X_{heat}$ = 100% * X(post-heat)/X(pre-heat);
ΔX = % $X_{heat}$(HARC/Steroid) − % $X_{heat}$(HARC/Ctrl);
In which X = G' or δ or η

Figure 2A:
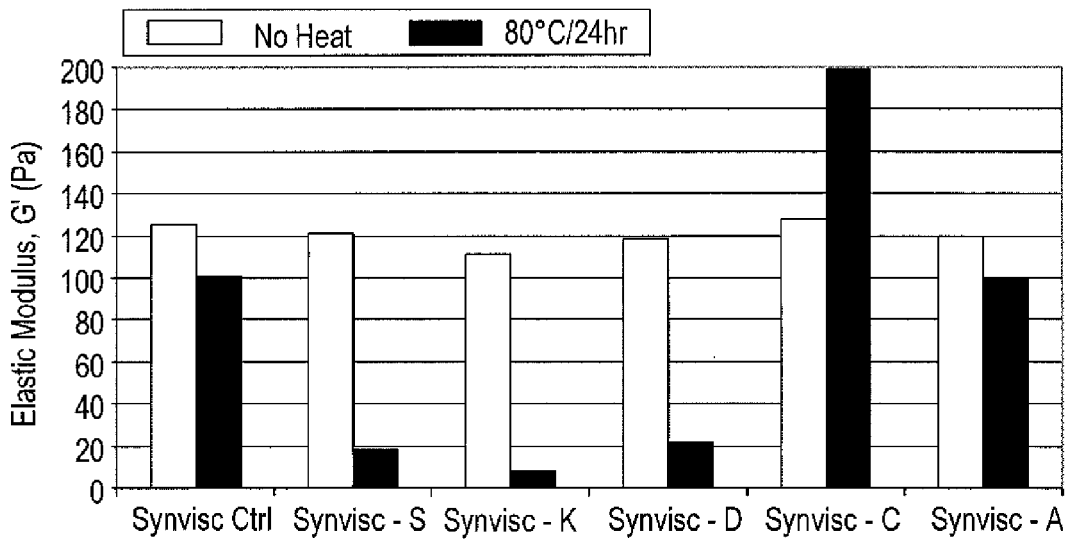
FIGS. 2a and 2b plot the change in elastic modulus after an accelerated shelf-life test (2a) and after sterilization (2b) for various HA/steroid formulations.
Figure 2B:
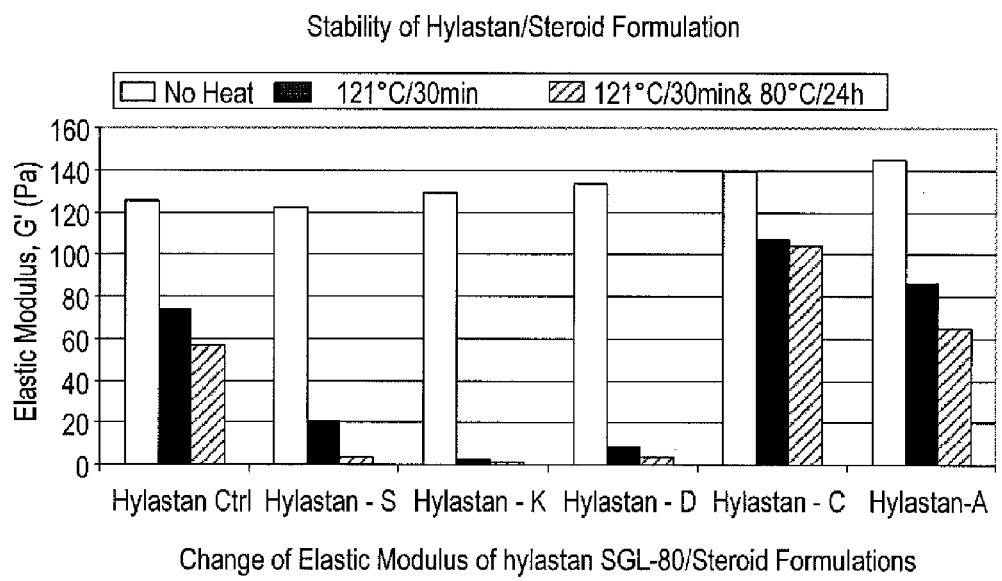

Of the formulations made with various steroids, TAH formulations behaved to comparably to control formulations having no steroid. Other steroid formulations we tested either: a) (in the case of triamcinolone acetonide, methyl prednisolone acetate, and betamethasone phosphate) exacerbated degradation of HARC properties after heat treatment, or b) (in the case of betamethasone acetate) interacted with HARC. The change in elastic modulus for different HA viscosupplement/steroid formulations are plotted in FIGS. 2a & 2b. Based on these experiments, we conclude that the TAH/HARC composition generally maintains a suitable level of stability when compared to the non-steroidal control.

pH and Osmolality

The pH and osmolality were measured and are listed in Tables 2a & 2b. Results also showed no significant change in pH and osmolality after mixing the TAH into the HA-based viscosupplements. Compositions retained suitable pH and osmolarity.

TABLE 2a

Osmolality and pH of Synvisc/Steroid Formulations

| Sample ID | Name of Steroid | Heat Treatment | pH | St. Dev | % $pH_{heat}$ | ΔpH (%) | Osmolality (mOsm) | St. Dev | (%) $Osm_{heat}$ | ΔOsm (%) |
|---|---|---|---|---|---|---|---|---|---|---|
| Synvisc Ctrl | No Steroid | No Heat | 7.10 | 0.04 | | | 311 | 0 | | |
| | | 80° C./24 hr | 7.19 | 0.01 | 101% | 0.0% | 315 | 2 | 101% | 0.0% |
| Synvisc - S | Betamethasone Phosphate | No Heat | 7.62 | 0.01 | | | 358 | 1 | | |
| | | 80° C./24 hr | 7.51 | 0.01 | 99% | −2.7% | 367 | 7 | 103% | 1.4% |
| Synvisc - K | Triamcinolone Acetonide | No Heat | 7.23 | 0.01 | | | 316 | 1 | | |
| | | 80° C./24 hr | 7.33 | 0.04 | 101% | 0.1% | 314 | 1 | 99% | −1.7% |
| Synvisc - D | Methylprednisolone Acetate | No Heat | 7.21 | 0.03 | | | 317 | 4 | | |
| | | 80° C./24 hr | 6.58 | 0.03 | 91% | −10.0% | 318 | 1 | 100% | −0.9% |
| Synvisc - C | Betamethasone Acetate | No Heat | 7.15 | 0.02 | | | 318 | 0 | | |
| | | 80° C./24 hr | 6.38 | 0.04 | 89% | −12.1% | 322 | 2 | 101% | 0.0% |
| Synvisc - A | Triamcinolone Hexacetonide | No Heat | 7.25 | 0.03 | | | 318 | 5 | | |
| | | 80° C./24 hr | 7.28 | 0.00 | 100% | −0.9% | 313 | 1 | 99% | −2.5% |

% $X_{heat}$ = 100% * X(post-heat)/X(pre-heat);
ΔX = % $X_{heat}$(HARC/Steroid) − % $X_{heat}$(HARC/Ctrl)
In which X = pH or Osmolality TABLE 2b Osmolality and pH of Hylastan/Steroid Formulations

| Sample ID | Name of Steroid | Heat treatment | pH | St. Dev | % $pH_{heat}$ | ΔpH (%) | Osmolality (mOsm) | St. Dev | % $Osm_{heat}$ | ΔOsm (%) |
|---|---|---|---|---|---|---|---|---|---|---|
| Hylastan Ctrl | No Steroid | No Heat | 7.27 | 0.01 | | | 339 | 3 | | |
| | | 121° C./30 min | 7.34 | 0.01 | 101% | 0.0% | 341 | 1 | 100% | 0.0% |

TABLE 2b-continued

Osmolality and pH of Hylastan/Steroid Formulations

| Sample ID | Name of Steroid | Heat treatment | pH | St. Dev | % pH$_{heat}$ | ΔpH (%) | Osmolality (mOsm) | St. Dev | % Osm$_{heat}$ | ΔOsm (%) |
|---|---|---|---|---|---|---|---|---|---|---|
| | | 121° C./30 min & 80° C./24 h | 7.34 | 0.01 | 100% | 0.0% | 340 | 1 | 100% | 0.0% |
| Hylastan - S | Betamethasone Phosphate | No Heat | 7.49 | 0.01 | | | 393 | 1 | | |
| | | 121° C./ 30 min | 7.43 | 0.01 | 99% | −1.7% | 380 | 3 | 97% | −3.7% |
| | | 121° C./30 min & 80° C./24 h | 7.36 | 0.01 | 99% | −0.9% | 383 | 3 | 101% | 1.1% |
| Hylastan - K | Triamcinolone Acetonide | No Heat | 7.28 | 0.01 | | | 344 | 4 | | |
| | | 121° C./30 min | 7.26 | 0.00 | 100% | −1.2% | 333 | 1 | 97% | −3.5% |
| | | 121° C./30 min & 80° C./24 h | 7.26 | 0.00 | 100% | 0.0% | 331 | 3 | 99% | −0.3% |
| Hylastan - D | Methyl prednisolone Acetate | No Heat | 7.31 | 0.01 | | | 342 | 0 | | |
| | | 121° C./30 min | 6.52 | 0.02 | 89% | −11.7% | 342 | 2 | 100% | −0.5% |
| | | 121° C./30 min & 80° C./24 h | 6.39 | 0.01 | 98% | −1.9% | 344 | 2 | 101% | 0.9% |
| Hylastan - C | Betamethasone Acetate | No Heat | 7.33 | 0.01 | | | 346 | 4 | | |
| | | 121° C./30 min | 6.74 | 0.01 | 92% | −8.9% | 346 | 6 | 100% | −0.3% |
| | | 121° C./30 min & 80° C./24 h | 6.66 | 0.01 | 99% | −1.3% | 344 | 0 | 99% | −0.3% |
| Hylastan - A | Triamcinolone Hexacetonide | No Heat | 7.31 | 0.01 | | | 341 | 1 | | |
| | | 121° C./30 min | 7.32 | 0.02 | 100% | −0.8% | 333 | 3 | 98% | −2.6% |
| | | 121° C./30 min & 80° C./24 h | 7.33 | 0.01 | 100% | 0.1% | 334 | 3 | 100% | 0.6% |

% X$_{heat}$ = 100% * X(post-heat)/X(pre-heat);
ΔX = % X$_{heat}$(HARC/Steroid) − % X$_{heat}$(HARC/Ctrl)
In which X = pH or Osmolality An HPLC assay was employed to assess the stability of the incorporated steroids. All steroid/viscosupplement formulations without heat treatment served as controls. After an 80° C./24 hr heat treatment (simulating two years of room temperature storage), compositions according to the invention showed suitable chemical integrity after this heat treatment.

Figure 3A:
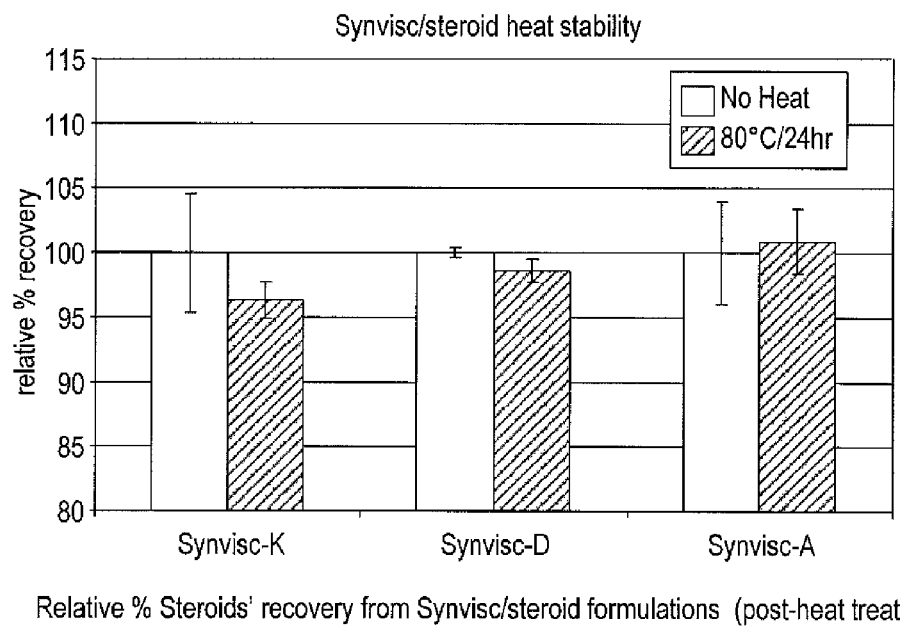
FIGS. 3a and 3b show the relative % of steroid recovery after heat treatment of various formulations.
Figure 3B:
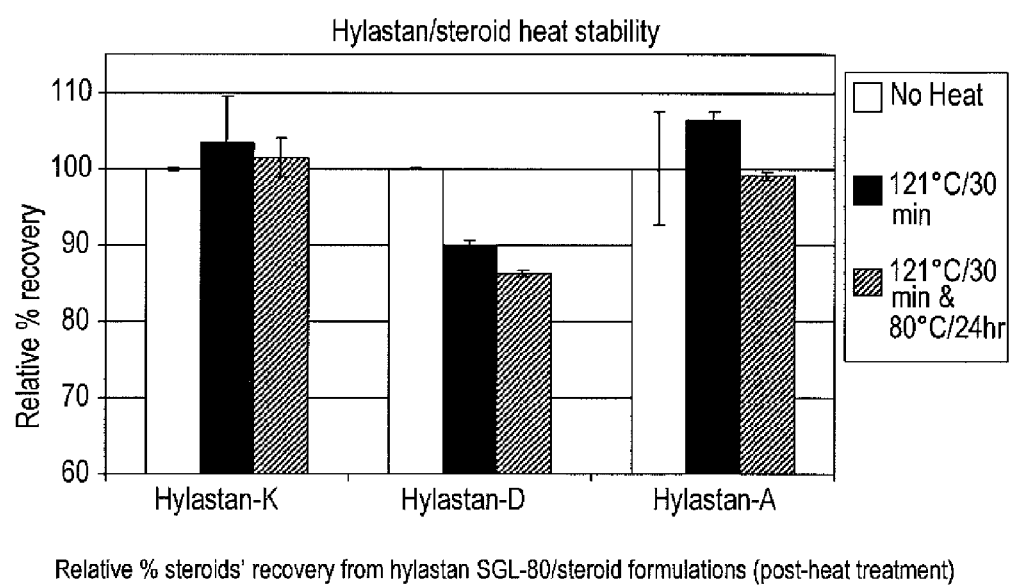

The relative % of steroid recovery for all steroid/viscosupplement formulations is shown in FIGS. 3a and 3b. It is unexpected the triamcinolone hexacetonide/viscosuplement combinational formulations are stable while the triamcinolone acetonide/viscosupplement formulations are not stable based on the rheology evaluation. These two steroids are very TABLE 3a Steroids' stability study for Synvisc/steroid formulations (heat treatment)

| Sample ID | Name of Steroid | Heat Treatment | Conc. of Steroid (mg/mL) | St. Dev. | Rel. % recovery | Std. Dev |
|---|---|---|---|---|---|---|
| Synvisc-K | Triamcinolone Acetonide | No Heat | 9.8 | 0.45 | 100 | 4.6 |
| | | 80° C./24 hr | 9.4 | 0.13 | 96.3 | 1.4 |
| Synvisc-D | Methylprednisolone Acetate | No Heat | 6.4 | 0.16 | 100 | 0.4 |
| | | 80° C./24 hr | 6.2 | 0.61 | 98.6 | 0.9 |
| Synvisc-A | Triamcinolone Hexacetonide | No Heat | 9.0 | 0.36 | 100 | 4.0 |
| | | 80° C./24 hr | 9.1 | 0.23 | 100.9 | 2.5 |

TABLE 3b

Steroids' stability study for hylastan SGL-80/steroid formulations (heat treatment)

| Sample ID | Name of Steroid | Heat Treatment | Conc. of Steroid (mg/mL) | St. Dev. | Rel. % recovery | Std. Dev |
|---|---|---|---|---|---|---|
| hylastan-K | Triamcinolone Acetonide | No Heat | 10.1 | 0.02 | 100 | 0.2 |
| | | 121° C./30 min | 10.5 | 0.63 | 103.3 | 6.2 |
| | | 121° C./30 min & 80 C./24 hr | 10.3 | 0.25 | 101.4 | 2.5 |
| hylastan-D | Methylprednisolone Acetate | No Heat | 8.2 | 0.01 | 100 | 0.1 |
| | | 121° C./30 min | 8.1 | 0.55 | 89.9 | 0.7 |
| | | 121° C./30 min & 80 C./24 hr | 6.6 | 0.23 | 86.2 | 0.4 |
| hylastan-A | Triamcinolone Hexacetonide | No Heat | 8.6 | 0.64 | 100 | 7.5 |
| | | 121° C./30 min | 9.2 | 0.08 | 106.4 | 1.0 |
| | | 121° C./30 min & 80 C./24 hr | 8.5 | 0.04 | 99.1 | 0.5 | similar chemically and large difference in stability would not be predicted.

The following examples illustrate the invention and those skilled in the art will readily understand that other embodiments may be made without departing from the spirit and scope of the invention.

Example 1

The composition will be a homogeneous colloidal suspension of triamcinolone hexacetonide, USP combined with an HA-based viscosupplement. The physical appearance will be a milky white viscous fluid. Product will be supplied sterile in a prefilled syringe (e.g, 5 mL with a 5 mL product fill).

| Formulation of Product in Pre-filled Syringe | |
|---|---|
| Component | Amount per mL |
| Triamcinolone hexacetonide, USP | 2 to 12 mg |
| Non-modified hyaluronic acid fluid (35% polymer content) | 3.5 mg |
| Cross linked hylastan gel (65% polymer content) | 6.5 mg |
| Polysorbate 80 | 0.35 mg |
| Sodium chloride | 8.47 mg |
| Sodium phosphate monobasic•$H_2O$ | 0.26 mg |
| Sodium phosphate dibasic•$7H_2O$ | 2.17 mg |
| Water for injection | QS to 1.0 ml |

Example 2

Gen-S1023-75 is a mixture of TAH (Triamcinolone Hexacetonide) with a HA based viscosupplement. The viscosupplement was made with DVS modified HA gel (AVS-gel) and unmodified HA fluid at 65:35 ratio of gel:fluid. Gen-S1023-75 contained about 8 mg/ml TAH (1002196), 0.35 mg/ml Tween-80 (Lot #E35595), 6.5 mg/ml of HA/DVS gel (lot #EX0848) and 3.5 mg/ml of unmodified HA.

| | Gen-S. Rheological Properties. | | | | | |
|---|---|---|---|---|---|---|
| | δ(5) (°) | St. Dev | G'(5) (Pa) | St. Dev | η(1) (Pas) | St. Dev |
| | | | Specification | | | |
| Sample ID | <35° | | 20-150 Pa | | 30-100 Pas | |
| Gen-S 1023-75 (post-autoc) | 21 | 0.7 | 86 | 2.8 | 70 | 8.5 |
| Gen-S 1023-75 24 hrs @ 80° C. | 34 | 2.1 | 36 | 3.5 | 43 | 3.5 |
| Gen-S 1023-75 (pre-autoc) | 16 | 0.0 | 108 | 1.4 | 81 | 4.2 |

Example 3

Experiments comparing the extrusion force required to deliver the composition from a 5 cc and a 10 cc syringe (compared to a composition lacking TAH) are summarized in the following table.

| Extrusion Data for Gen-S lots | | | | |
|---|---|---|---|---|
| Gen-S lot # | Description | Average extrusion force | | |
| | | Newtons | Syringe | Needles |
| | Extrusion force from a 5 cc syringe | | | |
| MTS 09020 | Gen-S + 0 mg/ml TAH | 15.4 | 5 cc | 20G 1.5" |
| MTS 09022 | Gen-S + 12 mg/ml TAH | 12.42 | 5 cc | 20G 1.5" |
| 1023-75 5 ml | Gen-S + 8 mg/ml TAH | 15.21 | 5 cc | 20G 1.5" |
| | Extrusion force from a 10 cc syringe | | | |
| 1023-68 | Gen-S + 2 mg/ml TAH | 22.87 | 10 cc | 20G 1.5" |
| 1023-70 | Gen-S + 8 mg/ml TAH | 22.39 | 10 cc | 20G 1.5" |
| 1023-75 5 ml | Gen-S + 8 mg/ml TAH | 16.42 | 10 cc | 20G 1.5" |
| 1023-75 6 ml | Gen-S + 8 mg/ml TAH | 17.62 | 10 cc | 20G 1.5" |
| | Comparison to 80:20 formulation | | | |
| MTS 03002-B | hylastan SGL-80 (Jonexa) 80% gel | 22.51 | 5 cc | 20G 1.5" |
| MTS 09020 | hylastan 65:35 w/PS 65% gel | 15.4 | 5 cc | 20G 1.5" |

Accordingly, these and other embodiments are within the scope of the following claims.

What is claimed is:

1. A method of making a sterile pharmaceutical composition packaged in a syringe, comprising an admixture of a hyaluronic acid related component (HARC) and a pharmaceutically effective amount of triamcinolone hexacetonide (TAH), the method comprising
mixing the HARC with the triamcinolone hexacetonide (TAH) to form an HARC/TAH mixture, the HARC comprising DVS-cross linked hyaluronic acid,
packaging said HARC/TAC mixture in a syringe,
subjecting the mixture to heat sterilization to form a sterile admixture, and
storing said syringe containing said sterile admixture,
said composition exhibiting both following characteristics a) and b) when compared in an accelerated shelf-life test to a control composition having said HARC but lacking TAH, said accelerated shelf-life test comprising heating at 80° C. for 24 hours:
a) the change in the elastic modulus (ΔG') of the composition is no more than 10% greater than ΔG' of the control composition;
b) the change in the viscosity (Δη) of the composition is no more than 10% greater than Δη of the control composition,
said composition having a viscosity between 20 Pas and 100 Pas.

2. The method of claim 1 in which the composition comprises at least 5 mg of HARC per ml of the composition.

3. The method of claim 1 in which the composition is sterile and has a viscosity of between 20 Pas and 100 Pas.

4. The method of claim 1 in which the composition has viscoelastic properties such that it is delivered from a 5 cc syringe with a needle size of 20G-1.5" with an extrusion force of less than 30 Newtons.

5. The method of claim 1 in which the composition is stable in an accelerated shelf-life test compared to a control composition having said HARC but lacking TAH, said accelerated shelf-life test comprising heating at 80° C. for 24 hours, and said composition exhibiting one or more of the following criteria:
- a) the composition retains at least 90% of its chemical integrity;
- b) the pH of the composition changes less than 0.5 pH units;
- c) the osmolality of the composition changes less than 3%.

6. The method of claim 1 in which the composition has a sterility suitable for human administration.

7. The method of claim 1 in which the composition further comprises a surfactant.

8. The method of claim 7 in which the surfactant is selected from the group consisting of Polysorbate 80, Polysorbate 20, Pluronic F-127, and Pluronic F-68.

9. The method of claim 1 in which the composition is inserted into a syringe and the syringe including the composition is heat sterilized.

10. The method of claim 1 in which the heat sterilization is in an autoclave.

* * * * *